(12) United States Patent
Kim

(10) Patent No.: US 8,632,588 B2
(45) Date of Patent: Jan. 21, 2014

(54) MITRAL VALVE CERCLARGE ANNULOPLASTY APPRATUS AND METHOD THEREOF

(76) Inventor: June-Hong Kim, Busan (KR)

(*) Notice: Subject to any disclaimer, the term of this patent is extended or adjusted under 35 U.S.C. 154(b) by 0 days.

(21) Appl. No.: 13/425,270

(22) Filed: Mar. 20, 2012

(65) Prior Publication Data

US 2012/0179246 A1   Jul. 12, 2012

Related U.S. Application Data

(63) Continuation-in-part of application No. 12/631,803, filed on Dec. 4, 2009, now Pat. No. 8,231,671.

(30) Foreign Application Priority Data

Aug. 12, 2011 (KR) .................. 10-2011-0080392

(51) Int. Cl.
*A61F 2/24* (2006.01)
(52) U.S. Cl.
USPC ....................................... 623/2.37; 623/2.36

(58) Field of Classification Search
USPC ................................................ 623/2.36–2.37
See application file for complete search history.

(56) References Cited

U.S. PATENT DOCUMENTS 6,217,610 B1* 4/2001 Carpentier et al. .......... 623/2.37
2002/0183838 A1* 12/2002 Liddicoat et al. ............ 623/2.11

* cited by examiner

*Primary Examiner* — Andrew Iwamaye
*Assistant Examiner* — Leslie Coburn
(74) *Attorney, Agent, or Firm* — Maxon IP LLC.; Justin H. Kim, Esq.

(57) ABSTRACT

A mitral cerclage annuloplasty apparatus comprises a tissue protective device and a cap device having a cerclage suture disposed within a first protective tube and a second protective tube, the proximal portions of the two tubes being attached side-by-side longitudinally to define a stem portion, the distal portions of the two tubes being separated thereafter, and a cap device that covers the stem portion wherein the stem portion and the cap device interlock, so that once the cerclage suture is knotted on the outer surface of the cap device, cap device can be pulled outwardly to enhance and maintain tension applied to the mitral annulus thus successfully treating the mitral regurgitation.

9 Claims, 10 Drawing Sheets

MITRAL VALVE CERCLARGE ANNULOPLASTY APPRATUS AND METHOD THEREOF

CROSS-REFERENCE TO RELATED APPLICATIONS

This application is a continuation-in-part of prior application Ser. No. 12/631,803, filed Dec. 4, 2009 and claims the benefit of a foreign priority of Korean Patent Application No. 10-2011-0080392, filed Aug. 12, 2011, which is incorporated herein in its entirety.

FIELD OF THE DISCLOSURE

The present disclosure relates to mitral valve cerclage annuloplasty devices and techniques in which during the final stage of cerclage annuloplasty procedure, a proper tension is applied and maintained safely on the cerclage sutures then firmly secured by using a knot tightening and securing device.

BACKGROUND OF THE INVENTION

The heart is the center of human circulatory system that pumps blood through our body. It is a muscle that pumps the blood only in one direction. In order for the heart to effectively maintain this unidirectional flow of blood, it must have properly functional valves that prevent back flow through its system, or regurgitation. The heart is divided into four chambers, right and left atria, and right and left ventricles. The four chambers are connected to the aorta, the inferior and superior vena cava, the pulmonary artery, and the pulmonary veins.

The mitral valve ("MV") separates the left atrium from the left ventricle while the tricuspid valve (TV) separates the right atrium from the right ventricle. The aortic valve ("AV") is located between the left ventricle and the aorta while the pulmonary valve ("PV") is located between the right ventricle and the pulmonary artery.

Generally, valves should open and close completely with every heart beat or contraction. Incomplete opening and closing of the valves cause improper flow of blood, either back flow and/or reduced. These are valvular diseases. The valvular diseases are divided into two categories, regurgitation and stenosis. Regurgitation is a failure of valve to close completely allowing back flow of blood. Stenosis is a failure of valve to open completely reducing the flow of blood. Both can increase stress on the heart.

Mitral valve regurgitation ("MVR") is a valvular disease in which an incomplete closure of the MV results in a back flow of blood. Such back flow of blood increases stress on the heart which can decrease the heart function and eventually lead to an irregular heart beat or a cardiac arrhythmia.

Traditional treatment of a worsening MVR requires an open heart surgery with a sternotomy or a thoracotomy then opening the heart itself following a cardiopulmonary bypass and a cardiac arrest. Once the chest is opened and access to the heart is gained, the MV is either repaired or replaced with an artificial valve. Although very effective, this open-heart procedure is an invasive high-risk surgery accompanied by a substantial morbidity and mortality. The mortality due to the surgery itself can be as high as 5%. Hence, the procedure is often reserved only to those patients with severe symptomatic MVR.

This high morbidity rate of the open heart surgery has recently lead to an increase in research to develop a safer and relatively more simple alternative procedures to repair the MVR using a cardiac catheterization technique. Along this international effort to find a safer alternative procedure, recently, this inventor presented internationally his thesis regarding "the mitral valve cerclage coronary sinus annuloplasty" and demonstrated outstanding result of the MVR treatment involving the application of a circular pressure around the mitral annulus (MA). This thesis has been filed through PCT as an international patent application (application number: PCT/ US2007/023836), and is currently published with the international patent office (publication number: WO2008/060553), which are incorporated herein in their entirety.

The aforementioned thesis and published patent applications disclose the mitral valve cerclage annuloplasty procedure. Briefly explained, a catheter is placed at the coronary sinus after accessing the right atrium through the jugular vein, and then a cerclage suture is passed through the proximal septal vein. This cerclage suture can easily pass through the right ventricular outflow tract ("RVOT"). The inventor defines this technique as "the simple mitral cerclage annuloplasty." Then the cerclage suture can be easily pulled into the right atrium thus placing the cerclage suture circumferentially around the MA. Once positioned, tension is applied to the cerclage suture and tightens the mitral valve. This brings together the two leaflets of the MV so that they are approximated to each other thus decreasing the size of its incomplete closure. This procedure can obtain a very similar result when compared to the result of a conventional surgery that directly tightens the mitral annulus, and can immediately reduce the regurgitation effectively treating a MVR.

However, there were technical problems in the previous thesis and patent applications that needed to be solved. First, there is a need to have a tension locking device that can apply a proper tension and maintain it securely during the procedure. Second, since this tension is maintained with a very fine cerclage suture i.e., 0.014 inch nylon cerclage used in the researches (although thickness may change), it can cause damages on the cardiac tissues where the suture contacts and exerts its pressure.

To address these technical problems, this inventor has filed Korean patent application (application number 2009-0080708) on Aug. 8, 2008, titled "the Mitral Valve Cerclage Annuloplasty Apparatus" that includes the coronary sinus and the tricuspid valve protection device, and a knot delivery device.

This patent application has also been filed with the U.S. Patent and Trademark Office and patent offices in other countries.

In the aforementioned patent application, the cardiac tissue is protected from the damage caused by the direct suture contact using a tissue protective device comprising a coronary sinus tube ("CS tube") and a tricuspid valve tube ("TV tube"). Further, a knot delivery device is used to place a knot at the end of the tissue protective device to complete the procedure.

However, even though the knot was placed at the end of the tissue protective device, a slack of suture remained between the end of the tissue protective device and the knot, so that the proper tension needed on the cerclage was difficult to obtain initially, and due to the remaining excess suture, the cerclage became loose.

In the aforementioned mitral valve cerclage annuloplasty procedure, when the cerclage suture became loose, the tension on the suture decreased thereby reducing its circumferential pressure applied around the MA resulting in a decreased effectiveness of the MVR treatment. This invention is intended to provide a viable solutions to overcome these problems.

SUMMARY OF THE INVENTION

The objective of this invention is to overcome the shortcomings of the aforementioned mitral valve cerclage annuloplasty apparatus by providing a device that can maintain a constant proper tension without creating a laxity on the cerclage suture thereby applying and maintaining a proper circumferential pressure around the MA and thus, increasing the effectiveness and the success of the mitral valve cerclage annuloplasty.

This invention achieves the aforementioned objectives by using a simple, easy to use devices described here that can initiate a proper knot placement and maintain its proper tension on the cerclage suture continuously.

Generally, to achieve its objective and overcome the shortcomings of the aforemetioned mitral valve cerclage annuloplasty apparatus, the current invention comprises a coronary sinus protective device 22, a tricuspid valve and ventricular wall protective device 24, a distal coronary sinus tissue protective tube, and a distal tricuspid valve protective tube that connects and becomes fixed, and a tissue protective device 20 with a built-in locking bumps 28 ingrained on the outside of the stem portion 26.

This invention further comprises a hollow cap 30 that fits over the tissue protective device 20 with an open distal end, a closed proximal end 31 with two or smaller openings 32 that allows passing of the cerclage sutures, and a built-in locking ridges 35 ingrained on the inside of the hollow cap 30 that interlocks with the stem-portion locking-bumps 28 of the tissue protective device 20.

The stem-portion locking-bumps 28 of the tissue protective device 20 and the cap locking ridges 35 interlock in such a manner that only allows the lengthening of the tissue protective device 20 and the hollow cap 30, and prevents shortening of the tissue protective device 20 and the hollow cap 30.

According to the current invention, a ring-hook 34 that allows a suture to be passed through is located at the distal end of the hollow cap 30.

In a first embodiment, the stem-portion locking-bumps 28 of the tissue protective device 20 and the cap locking ridges 35 are in a shape of a saw-tooth.

In a second embodiment, the stem-portion locking-bumps 28 of the tissue protective device 20 is in a shape of a saw-tooth, and the cap locking ridges 35 are formed by equally spaced slits corresponding to the stem-portion locking-bumps 28.

In a third embodiment, the hollow cap 30 comprises a cap body 38 and a cap lid 36 such that a neck 36a of the cap lid inserts into the cap body 38.

In a fourth embodiment, the inside of the cap body 38 and the out side of the neck of the cap lid 36a is in the shape of a screw such that cap can be screwed into the cap body.

In a fifth embodiment, the stem-portion locking-bumps 28 of the tissue protective device 20 can be disposed on the two sides of the stem portion rather than surrounding the entire stem circumferentially.

As described above, the current invention improves the mitral valve cerclage annuloplasty apparatus by adding the hollow cap 30 to the tissue protective device 20. The hollow cap 30 holds the cerclage suture knot in place while persistently maintaining a proper tension. When a persistent proper tension on the cerclage suture is maintained without laxity, a proper circumferential pressure around the MA can be sustained continuously thus, increasing the effectiveness and the success of the mitral valve cerclage annuloplasty.

BRIEF DESCRIPTION OF THE DRAWINGS

FIG. 1 shows the tissue protective device and the hollow cap before the cap is placed onto the tissue protective device, and FIG. 2 shows the hollow cap fitted onto the tissue protective device.

FIG. 3 shows the cerclage suture knot placed outside the hollow cap. FIG. 4 shows the hollow cap being pulled outwardly from the stem portion of the tissue protective device while the cerclage suture knot is caught and supported by the closed distal end of the hollow cap. FIG. 5 shows cutting and removing of the excess cerclage suture distal to the knot, and removing the cap pulling suture.

DETAILED DESCRIPTION OF THE INVENTION

The detailed disclosure of the mitral valve cerclage annuloplasty apparatus (MVA) comprising a tissue protective device and a hollow cap will be discussed.

Figure 1:
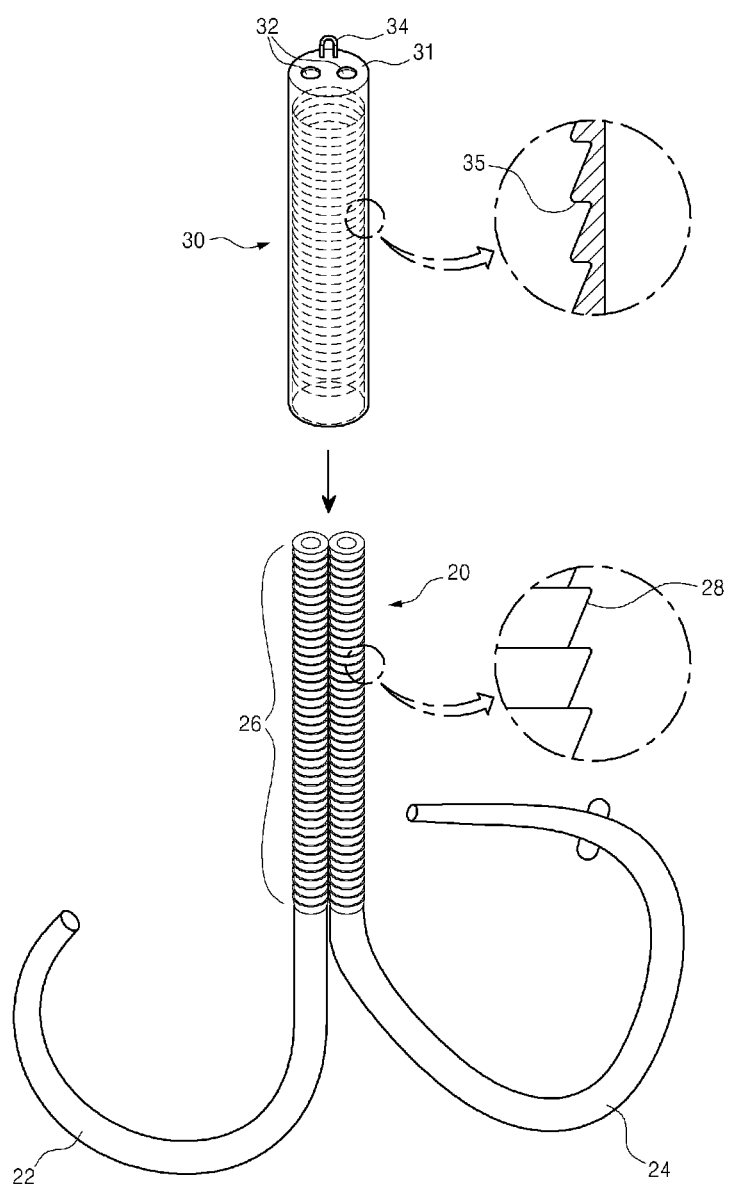
FIG. 1 and FIG. 2 show the mitral valve cerclage annuloplasty apparatus comprising a tissue protective device and a hollow cap.
Figure 2:
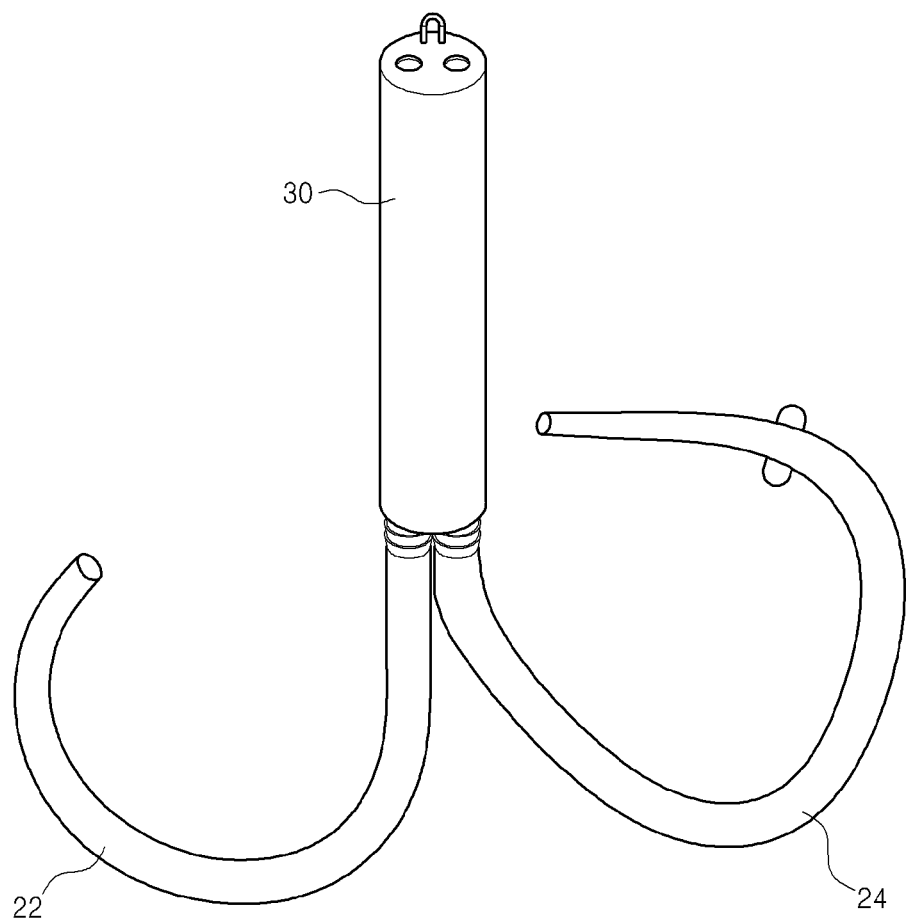

According to the current invention, FIGS. 1-2 shows the mitral valve cerclage annuloplasty apparatus (MVA) comprising the tissue protective device 20 and the hollow cap 30. FIG. 1 shows the tissue protective device 20 and the hollow cap 30 before they are engaged, and FIG. 2 shows the tissue protective device 20 and the hollow cap 30 in an engaged state. The tissue protective device 20 in the current invention differs from the inventor's previous patent application (#2009-0080708) in that the stem portion of the tissue protective device 20 has a built-in locking bumps 28 ingrained on its outer surface.

Generally, in a conventional MVA techniques cause tissue damage or erosion to the coronary sinus ("CS"), the tricuspid valve ("TV") and the intraventricular septum ("IVS") from a direct cerclage suture to tissue contact. These critical structures can be protected from damage by using the tissue protective device 20 comprising hollow tubes that allows passing of the cerclage suture preventing the direct contact of the suture onto the CS, the TV and the IVS tissues. Accordingly, the tissue protective device 20 comprises of a coronary sinus tube 22 ("CS tube") that protects the CS tissue, a tricuspid valve tube 24 ("TV tube") that protects the TV tissue and the IVS tissue, and a stem portion 26 with locking bumps 28 ingrained on its outer surface.

The inside of the cap 30 is hollow to allow insertion of the stem portion 26 of the tissue protective device 20, and it has an ingrained locking ridges 35 on its inside that interlocks with the locking bumps 28 ingrained on the outer surface of the stem portion 26.

The locking bumps 28 on the stem portion 26 and the locking ridges 35 ingrained on the inside of the hollow cap 30 are made so that they interlock in a way that allows only the outward movement of the hollow cap 30 while preventing the inward movement of the hollow cap 30. Thus, during the procedure, once a knot is made with the cerclage suture, the hollow cap 30 can be advanced outwardly to remove any laxity in the cerclage suture and then continuously maintain a proper tension on the cerclage suture.

To maintain the proper tension, the preferred shape of the stem-portion locking bumps 28 and the cap locking ridges 35 is that of a saw-tooth.

The hollow cap 30 comprises a closed proximal end 31 with two or more small openings 32. The purpose of the closed proximal end 31 is to support a cerclage-suture knot in place when the cap 30 is moved outwardly, and the purpose of the small openings 32 is to allow passage of the cerclage suture.

Further, on the outer surface of the closed proximal end 31 of the hollow cap 30 comprises a ring hook 34 for attaching a cap-pulling suture used to pull the cap 30 outwardly.

Figure 3:
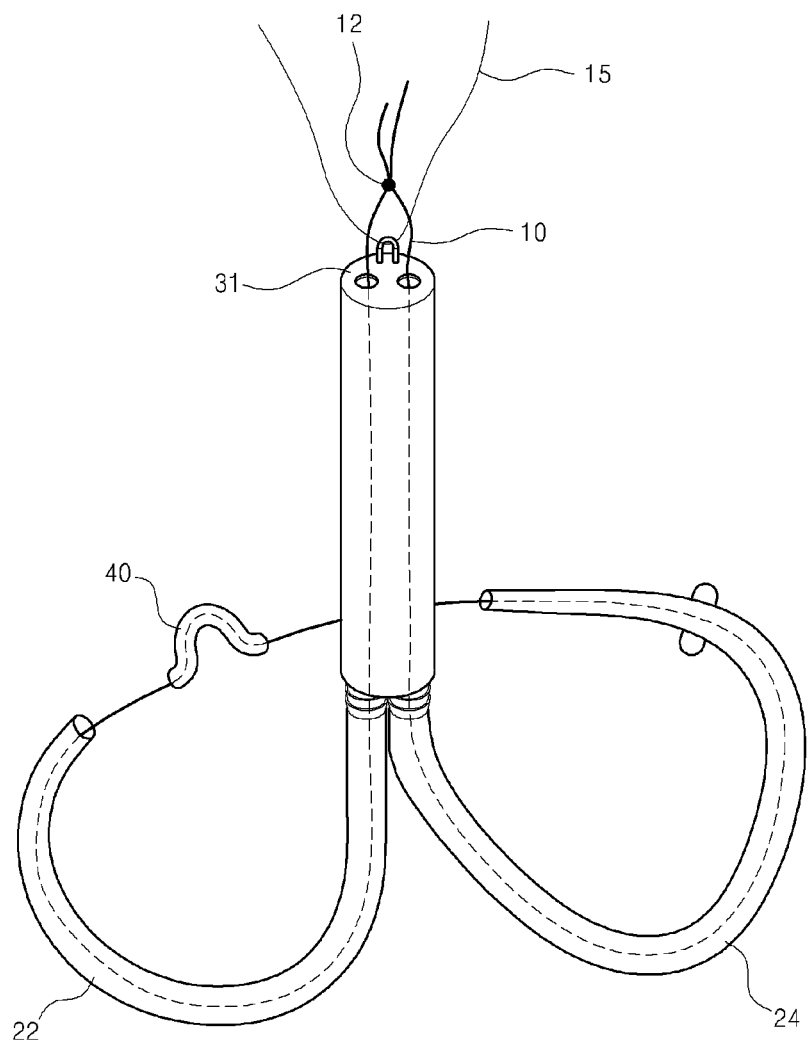
FIG. 3 through FIG. 5 show the mitral valve cerclage annuloplasty apparatus in operation with the cerclage suture.
Figure 4:
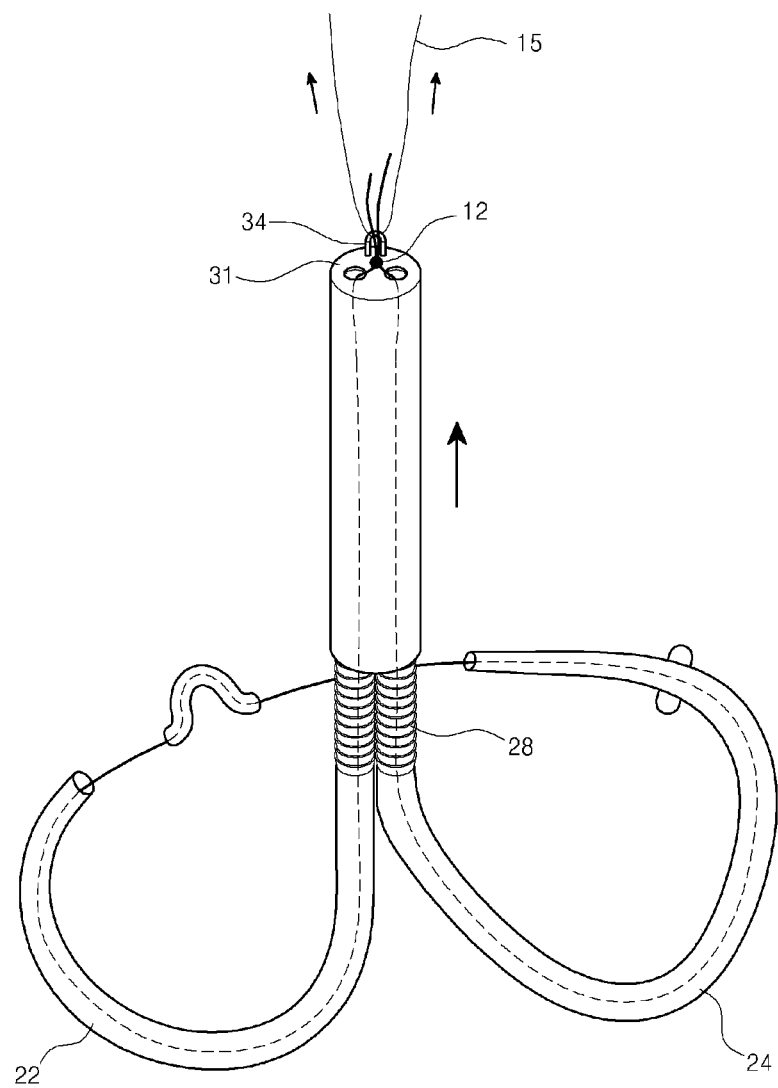
Figure 5:
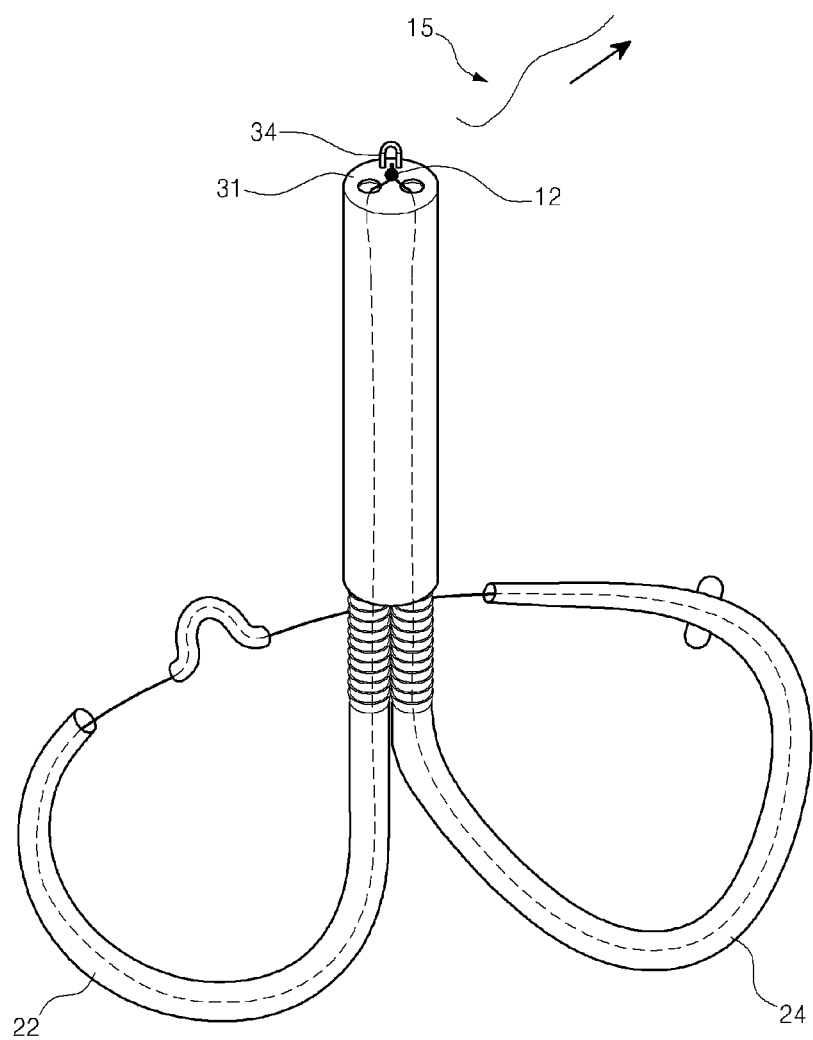

FIGS. 3-5 show operations of the MVA. FIG. 3 shows the cerclage-suture knot 12 made with a cerclage suture 10. FIG. 4 shows the cerclage-suture knot 12 supported by the closed proximal end 31 as the cap 30 is moved outwardly using the cap-pulling suture 15. FIG. 5 shows the cerclage-suture knot 12 after the excess cerclage suture has been cut proximal to the knot and removed, and removing of the cap-pulling suture 15.

In the cerclage annuloplasty procedure, once a proper circumferential pressure is applied onto the mitral valve with the cerclage suture 10 using the MVA of the current invention, a knot delivery device introduced by the inventor in his previous patent application (#2009-008070808) can be used to make the cerclage-suture knot 12. In this state as shown in FIG. 3, because the cerclage-suture knot 12 is not tight against the hollow cap 30, it is difficult to maintain the proper tension on the cerclage suture 10.

The cap-pulling suture 15 is first looped around the ring hook 34 of the hollow cap 30, then it is extended proximally to outside the body. The purpose of the cap-pulling suture 15 is to pull the hollow cap 30 outwardly.

Once the cerclage-suture knot 12 is made as shown in FIG. 4, when the cap-pulling suture 15 looped around the ring hook 34 is pulled from outside the body, as shown in FIG. 5, the hollow cap 30 will move outwardly. Since the cerclage-suture knot 12 is caught and supported by the closed distal end 31 of the hollow cap 30, the cap-pulling suture 15 can pull the hollow cap 30 moving it outwardly until the proper tension on the cerclage suture is obtained. As the hollow cap 30 is pulled outwardly, the locking bumps 28 on the stem-potion of the tissue protective device 20 and the cap locking ridges 35 interlock in a way such that they only allow outward movement of the hollow cap 30 and prevent its inward movement. Hence, even if the cap-pulling suture 15 no longer pulls on the cap outwardly, the hollow cap 30 will not advance inwardly.

As shown in FIG. 4, when the proper tension is obtained on the cerclage suture 10 by moving the hollow cap 30 outwardly, since the cerclage-suture knot 12 is caught and supported by the closed distal end 31, the circumferential pressure applied around the mitral annulus can be maintained constantly. Hence, the MVR of a patient is eliminated increasing the effectiveness and the success of the mitral valve cerclage annuloplasty.

As shown in FIG. 5, after cutting the cerclage suture 10 at a certain distance from the cerclage-suture knot 12 using a cutter (not illustrated here), the remaining excess cerclage suture can be taken out of the body, and the cap-pulling suture 15 can also be pulled out of the body. Hence, the mitral valve cerclage annuloplasty procedure is completed.

According to the current mitral valve cerclage annuloplasty apparatus, before starting the mitral valve annuloplasty procedure, the tissue protective device 20 must be inserted fully into the hollow cap 30. Due to the way in which the stem-portion locking bumps 28 of the tissue protective device 20 and the cap locking ridges 35 interlock, it can be difficult to engage the tissue protective device 20 fully into the hollow cap 30.

Figure 6:
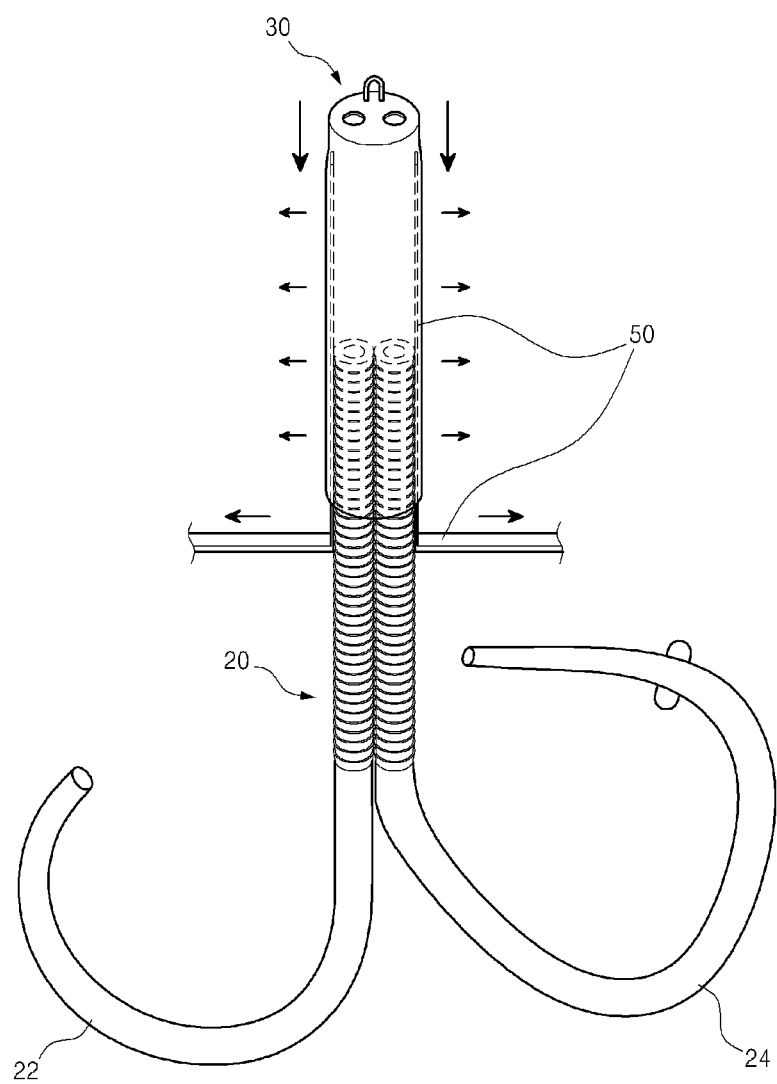
FIG. 6 shows the process in which the tissue protective device and the hollow cap become engaged in a first embodiment of the mitral valve cerclage annuloplasty apparatus.

There are various ways to fully engage the hollow cap 30 with the tissue protective device 20. FIG. 6 shows one of these methods where an expander 50 is used to help engage the hollow cap 30 with the tissue protective device 20.

The expander 50 is made in an L-shape with a handle bar 50a and an expander bar 50b. The expander bar 50b is inserted into the hollow cap 30, and the handle bar 50a is used to apply force needed to expand the hollow cap 30. The expander 50 is used to expand the inside space of the hollow cap 30 to allow easier entry of the tissue protective device 20. The hollow cap 30 can be made of a soft or a silk-like material. If the hollow cap 30 is made of a soft material, the expander 50 can be used to expand the inside space of the hollow cap 30 so that the tissue protective device 20 can be inserted into the hollow cap 30.

Three or more expanders 50 are used together to expand the inside space of the hollow cap 30 so that when they are pulled in opposing directions, the inside space of the hollow cap 30 is expanded to allow easier entry of the tissue protective device 20.

Once the tissue protective device 20 is fully inserted into the hollow cap 30, the expanders 50 return to their original position and are removed from the hollow cap 30 thereby achieving their purpose of helping engage the tissue protective device 20 with the hollow cap 30.

The expanders 50 can be installed on an expander device (not displayed) which can be operated using a motor or cylinder (not displayed). The expander device is used to operate the expanders 50 so that the expanders can expand or reduce the hollow cap 30.

Figure 7:
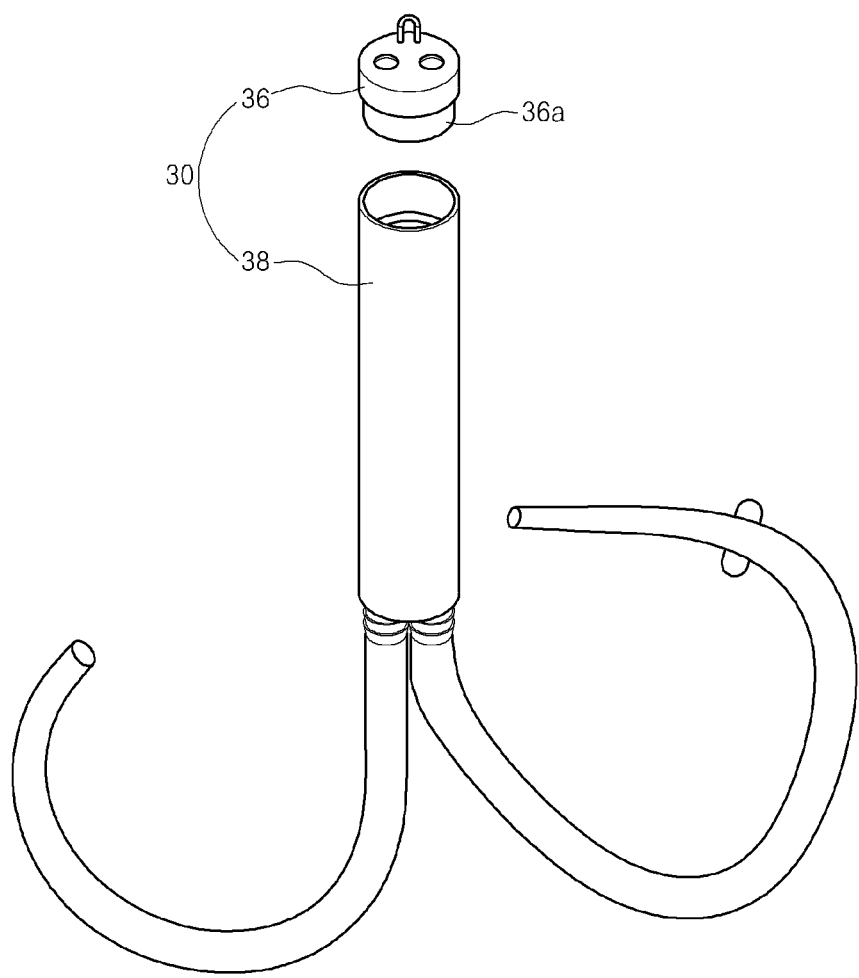
FIG. 7 shows a second embodiment of the mitral valve cerclage annuloplasty apparatus with a different cap configuration.

FIG. 7 shows another method of inserting the tissue protective device 20 into the hollow cap 30 where the hollow cap 30 is further divided into a cap body 38 and a cap lid 36. The cap body 38 and the cap lid 36 can be joined or separated.

As shown in FIG. 7, the cap body 38 and the cap lid 36 of hollow cap 30 are configured so that they can be joined or separated. The distal end of the cap lid 36 is formed as a cap-lid neck 36a so that it can be inserted into the cap body 38. In other words, when the cap lid 36 is separated from the cap body 38, the cap-lid neck 36a can be inserted into the cap body 38 so that the cap lid 36 and the cap body 38 can be become one.

First, the cap body 38 is separated from the cap lid 36. Then the two distal tubes of the tissue protective device 20 (the coronary sinus tube 22 and the tricuspid valve tube 24) are inserted into the cap body 38 through its upper portion. The tissue protective device 20 is then pulled through the cap body 38 until the stem portion of the tissue protective device is covered by the cap body 38. Then the cap lid 36 is inserted into the cap body 38 thus uniting the tissue protective device 20 and the hollow cap 30. An adhesive can be used to firmly secure the cap lid 38 to the cap body 36.

Figure 8:
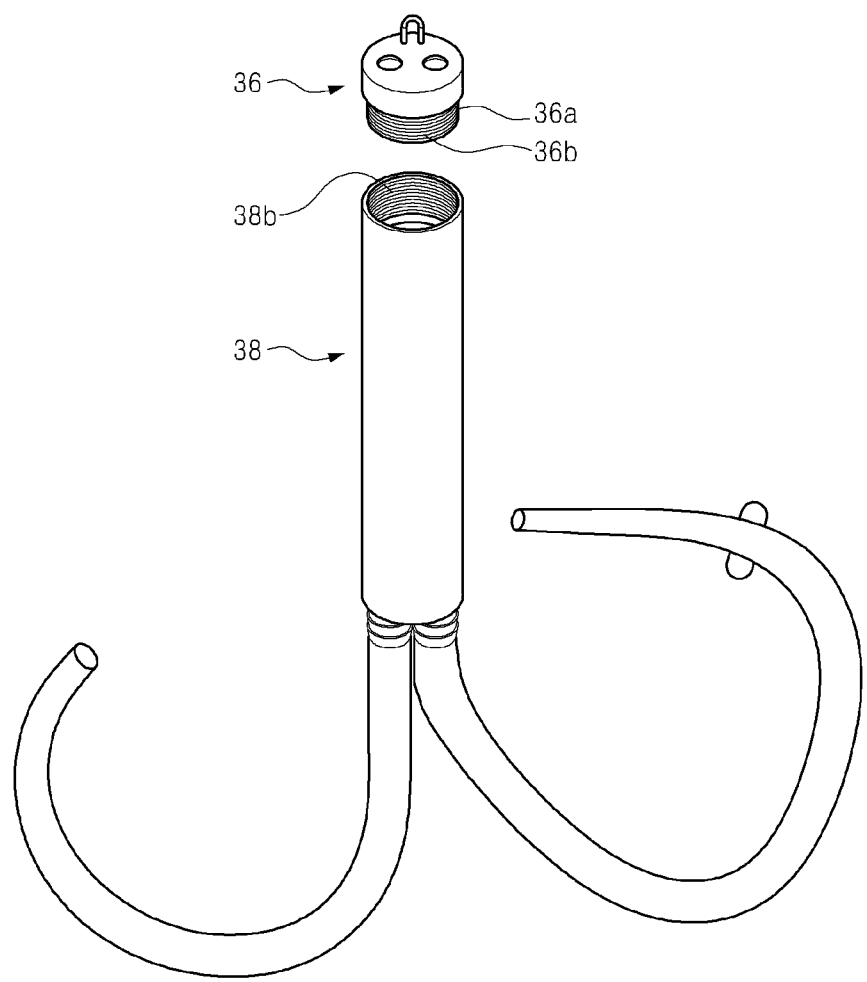
FIG. 8 shows a third embodiment of the mitral valve cerclage annuloplasty apparatus with another cap configuration.

FIG. 8 shows another embodiment of the hollow cap 30 with its detachable cap lid 36 and the cap body 38. The outer surface of the cap lid neck 36a has screw-like cap-lid thread 36b, and the inside of the cap body 38 has its corresponding cap-body receiving thread 38b. Hence, the cap lid 36 can be screwed into the lid body 38.

Figure 9:
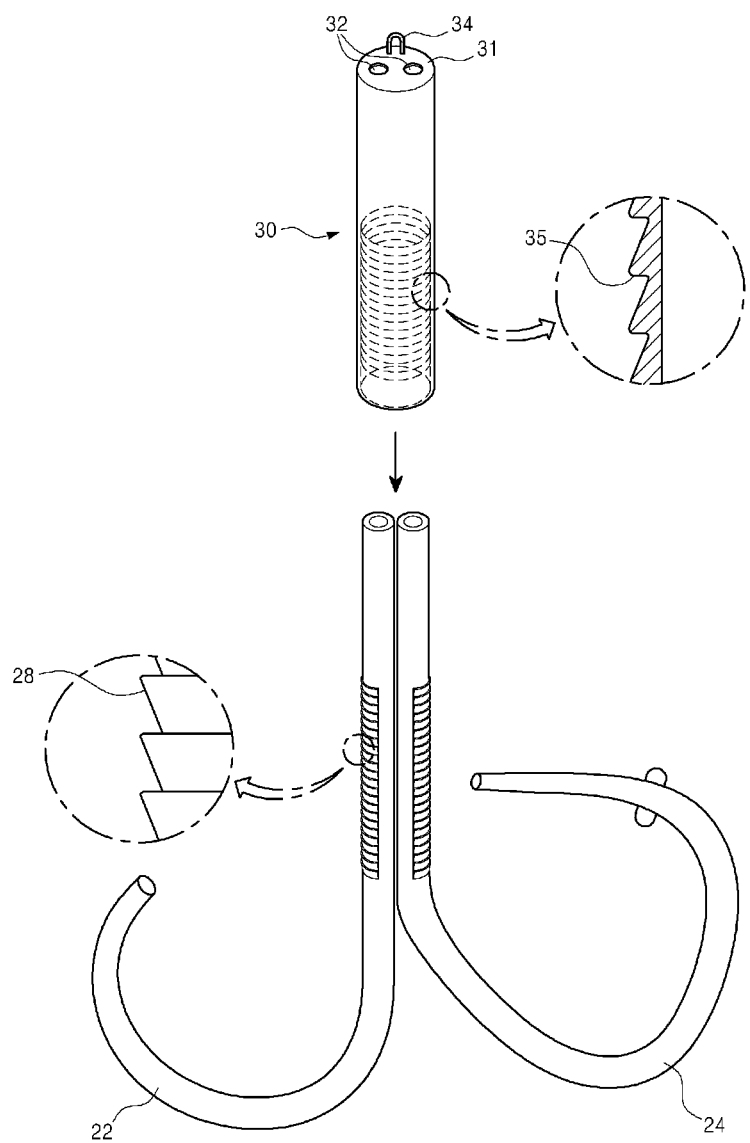
FIG. 9 shows a different configuration of the locking-bumps on the stem portion of the tissue protective device and the locking ridges in the hollow cap of the mitral valve cerclage annuloplasty apparatus.

FIG. 9 shows another embodiment of the mitral valve cerclage annuloplasty apparatus with a different distribution of the stem-portion locking bumps 28 of the tissue protective device 20, and the cap locking ridges 35.

FIG. 9 shows the locking bumps 28 ingrained on a part of the stem portion of the tissue protective device 20 rather than over the entire length of the stem portion. Specifically, the locking bumps 28 can be ingrained only on the sides of the stem portion of the tissue protective device 20. As shown in FIG. 9, the cap locking ridges 35 can also be ingrained on part of the hollow cap 30 rather than on the entire inside surface. The purpose of ingraining the locking bumps 28 only the sides of the stem portion of the tissue protective device is to facilitate easier flow of the blood.

Figure 10:
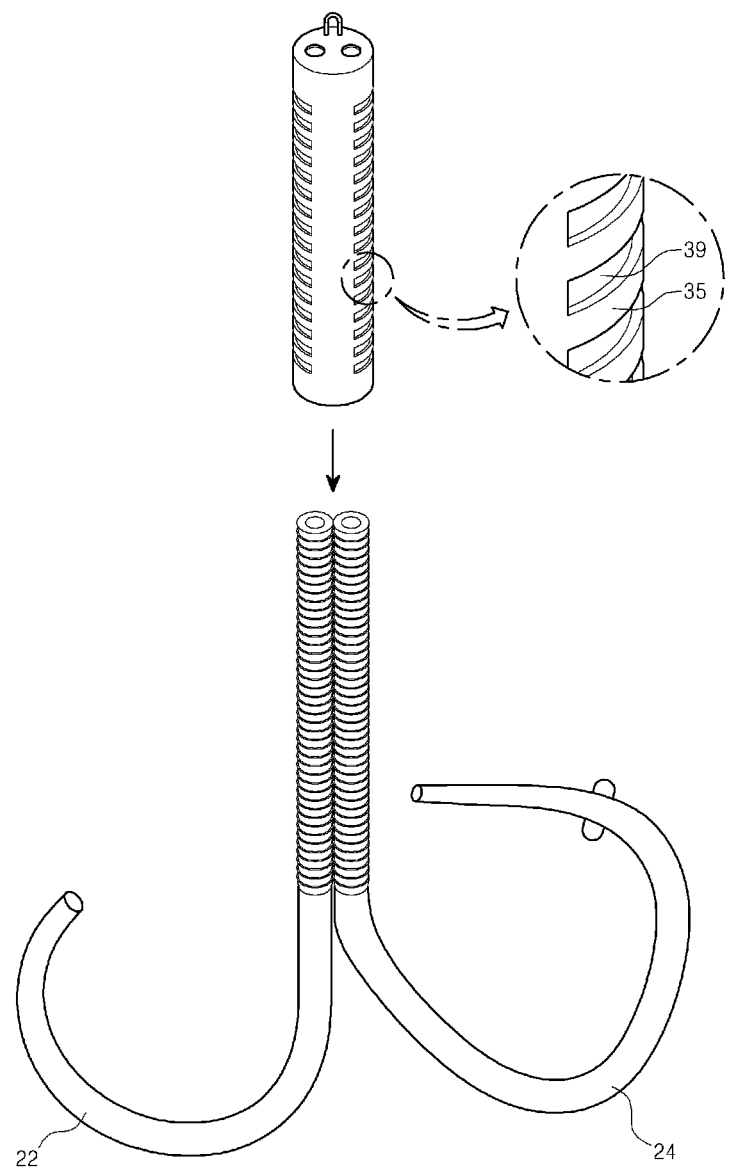
FIG. 10 shows another configuration of locking-bumps on the stem portion of the tissue protective device and the locking ridges in the hollow cap of the mitral valve cerclage annuloplasty apparatus.

FIG. 10 shows another embodiment of the mitral valve cerclage annuloplasty apparatus with a different shape of the cap locking ridges 35. FIG. 9 shows the cap locking ridges 35 inside the hollow cap 30 made of equally spaced open slits 39.

While the invention has been described in terms of specific embodiments, it is apparent that other forms could be adopted by one skilled in the art. Accordingly, it should be understood that the invention is not limited to the specific embodiments illustrated in the Figures. It should also be understood that the phraseology and terminology employed above are for the purpose of disclosing the illustrated embodiments, and do not necessarily serve as limitations to the scope of the invention.

The invention claimed is:

1. A device for mitral valve annuloplasty, comprising:
a tissue protective device, the tissue protective device having a cerclage suture disposed within a first protective tube and a second protective tube, the first protective tube and the second protective tube each having a proximal portion and a distal portion, the proximal portions of the two protective tubes being attached side-by-side longitudinally at least along a length thereof to define a stem portion, the distal portions of the two protective tubes being separated thereafter; and
a cap device that covers the stem portion wherein the stem portion and the cap device interlock.

2. The device according to claim 1, wherein the stem portion of the tissue protective device has ingrained locking bumps, and the inside of the cap device has ingrained locking ridges such that when the cap device covers the tissue protective device, the cap device and the tissue protective device interlock in a way that allows the outward movement of the cap device while preventing the inward movement of the cap device.

3. The device according to claim 2, wherein the ingrained locking bumps and the cap locking ridges are in a saw-tooth shape to interlock with each other.

4. The device according to claim 2, wherein the ingrained locking bumps are ingrained on a part of the stem portion, and the cap ridges are ingrained on a part of the inside of the cap device.

5. The device according to claim 2, wherein the cap locking ridges are in form of open slits that are equally spaced apart.

6. The device according to claim 1, wherein the cap device comprises a distal end plate, the distal end plate having at least two openings and a ring hook, the at least two openings allow passage of the cerclage suture therethrough and wherein the ring hook allows the passage of a cap pulling suture.

7. The device according to claim 1, wherein the cap device further comprises a cap lid and a cap body.

8. The device according to claim 7, wherein the cap lid and the cap body are secured to one another by rotating the cap lid and the cap body relative to one another.

9. The device according to claim 1, further comprising a set of expanders wherein the expanders are used to expand the cap device to facilitate easier insertion of the tissue protective device into the cap device.

\* \* \* \* \*